United States Patent [19]
Katzman et al.

[11] Patent Number: 5,750,074
[45] Date of Patent: May 12, 1998

[54] REAGENT SEGMENT

[75] Inventors: Steven P. Katzman, Yorba Linda; Ronald C. Glenday, Fullerton, both of Calif.

[73] Assignee: Beckman Instruments, Inc., Fullerton, Calif.

[21] Appl. No.: 376,574

[22] Filed: Jan. 23, 1995

[51] Int. Cl.[6] .......................... G01N 27/447; B01L 3/00
[52] U.S. Cl. .......................... 422/102; 422/63; 422/64; 422/68.1; 422/163; 436/43; 204/299 R; 220/571
[58] Field of Search .................... 422/63, 64, 67, 422/68.1, 99, 102, 103; 436/43; 204/299 R, 180.1, 601, 451; 220/571; 206/204

[56] References Cited

U.S. PATENT DOCUMENTS

| | | | |
|---|---|---|---|
| 3,441,383 | 4/1969 | Moore | 422/102 |
| 3,536,449 | 10/1970 | Astle | 436/179 |
| 3,540,858 | 11/1970 | Rochte et al. | 422/101 |
| 3,680,967 | 8/1972 | Engelhardt | 356/246 |
| 3,713,771 | 1/1973 | Taylor et al. | 436/48 |
| 3,713,985 | 1/1973 | Astle | 435/33 |
| 4,150,763 | 4/1979 | Simpson | 220/571 |
| 4,287,155 | 9/1981 | Tersteeg et al. | 422/64 |
| 4,298,570 | 11/1981 | Lillig et al. | 422/64 |
| 4,364,903 | 12/1982 | Bittings | 422/102 X |
| 4,471,297 | 9/1984 | Berg | 422/64 X |
| 4,551,311 | 11/1985 | Lorenz | 422/300 |
| 4,651,887 | 3/1987 | Patrick | 220/571 |
| 4,695,430 | 9/1987 | Coville et al. | 422/65 |
| 4,747,919 | 5/1988 | Anderson | 204/182.8 |
| 4,900,513 | 2/1990 | Barker et al. | 422/64 |
| 4,908,320 | 3/1990 | Zakowski et al. | 422/64 X |
| 5,005,721 | 4/1991 | Jordan | 220/23.4 |
| 5,051,238 | 9/1991 | Umetsu et al. | 422/64 |
| 5,061,381 | 10/1991 | Burd | 422/102 X |
| 5,145,646 | 9/1992 | Tyranski | 422/102 |
| 5,324,401 | 6/1994 | Yeung et al. | 204/180.1 |
| 5,339,676 | 8/1994 | Johnson | 220/571 |
| 5,356,525 | 10/1994 | Goodale et al. | 204/602 |
| 5,372,274 | 12/1994 | Freedland | 220/571 |
| 5,384,024 | 1/1995 | Moving et al. | 204/602 |
| 5,429,236 | 7/1995 | Evans | 220/571 |
| 5,474,205 | 12/1995 | Lancaster | 220/571 |

FOREIGN PATENT DOCUMENTS

| | | |
|---|---|---|
| 0100663 | 2/1984 | European Pat. Off. . |
| 0252632A2 | 6/1987 | European Pat. Off. . |
| 0415307 | 8/1990 | European Pat. Off. . |
| 0329579 | 2/1989 | France . |
| 0204109 | 4/1986 | Germany . |
| 8705533 | 9/1987 | WIPO . |
| 9220448 | 11/1992 | WIPO . |
| 9429024 | 12/1994 | WIPO . |

*Primary Examiner*—Long V. Le
*Attorney, Agent, or Firm*—William H. May; Gary T. Hampson; Sheldon & Mak

[57] ABSTRACT

A reagent segment including a body and trough formed therein with the floor of the trough sloped towards a drainage zone. The reagent segment is adapted for transporting reagents within an automated analyzer by having at least two protrusions on the exterior wall of the trough that fit within corresponding cavities of a transport arm. The reagent segment is retained by a latching mechanism through a protuberance on the exterior surface of the trough that conforms with a hole in the latching mechanism. The reagent segment can also have a concave depression on the interior surface of the trough at the drainage zone. The depression can coincide with the protuberance on the exterior surface of the trough that associates with the hole in the latching mechanism. Further, the reagent segment may include at least one indexing rib, between the exterior surface of the trough and the rim of the body, that can be inserted within an indexing slot of a holding means. Thus, the reagent segment is uniquely adapted for automated handling and processing of reagents in an automated analyzer.

20 Claims, 5 Drawing Sheets

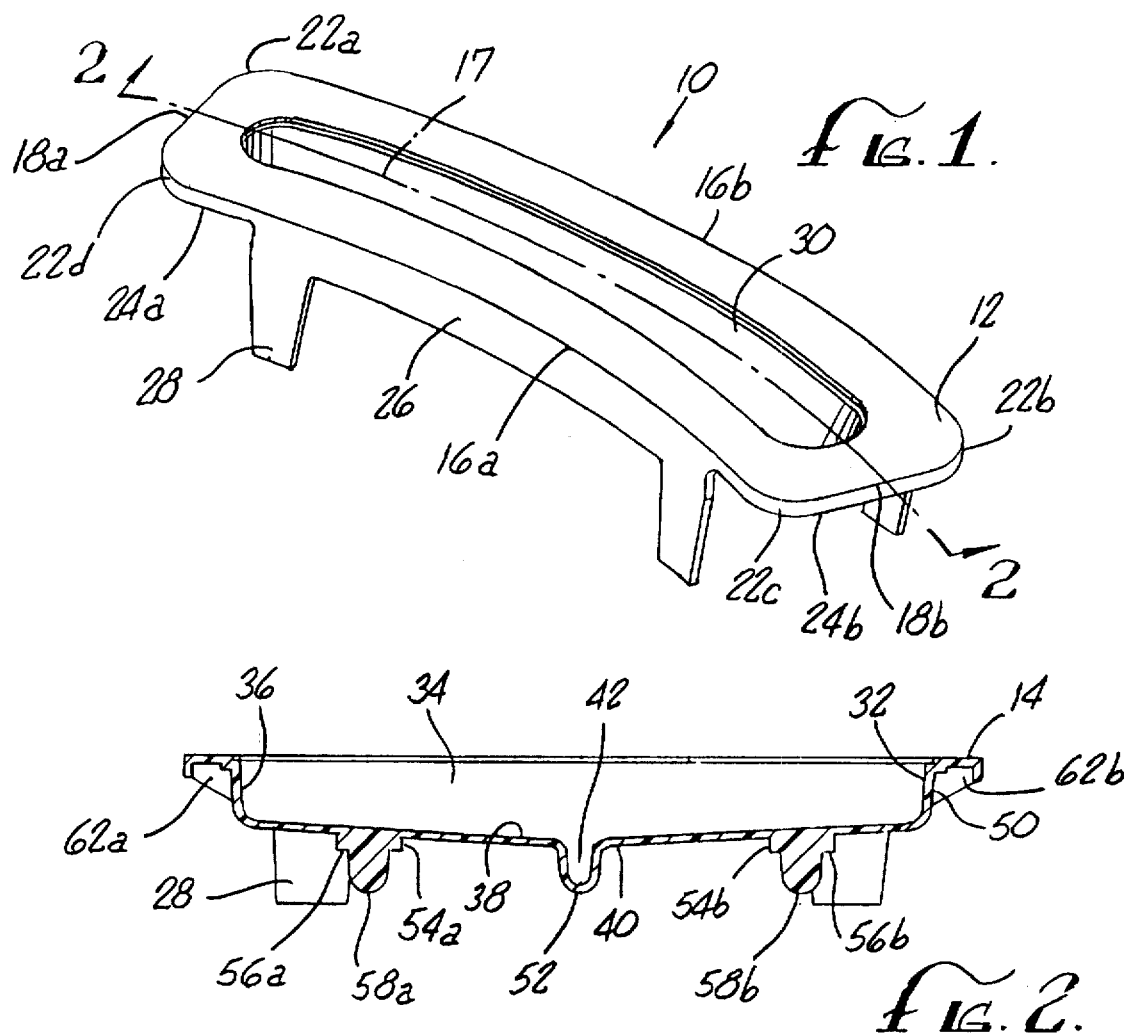

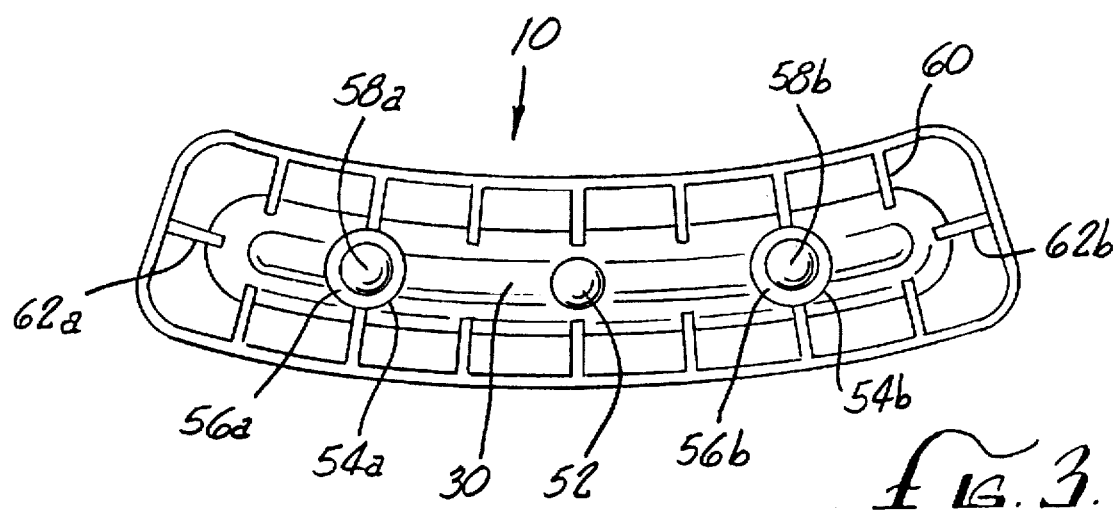

REAGENT SEGMENT

RELATED APPLICATIONS

The present application is related to the following applications that are commonly assigned and filed concurrently herewith, and which are incorporated herein by reference:

U.S. Pat. No. 5,356,525, entitled "Sample Handling System", filed in the names of David L. Goodale and Steven D. Mack, which is a continuation of U.S. patent application Ser. No. 08/048,708, filed Apr. 16, 1993 now abandoned;

U.S. patent application Ser. No. 08/071,831 filed Jun. 3, 1993, now abandoned, entitled "Sample Segment", filed in the names of Ronald C. Glenday, David L. Goodale and Steven D. Mack, which is a continuation of U.S. patent application Ser. No. 08/048,716, filed Apr. 16, 1993 now abandoned; and Certain inventive features In the present application are derived, in part, from the above-identified applications.

BACKGROUND

The development of automated sample handling systems for the processing and analysis of biological fluids has led to a variety of sample or reagent carrying devices. In general, some combination of a sample holder and a conveying means is used to transport a plurality of wells, cups, tubes or other containers to processing stations where various operational steps are performed. The sample receptacles can be self-aligning and self-retaining when positioned on an indexable unit, such as a turntable.

For example, U.S. Pat. No. 4,287,155 (Tersteeg et al.), describes a circular tray and carrier combination adapted to be mounted on a chemical analysis apparatus. The sample tray is formed of multiple arc-shaped segments. The segments have two rows of radially aligned holes, which receive replaceable sample cups or pipette tips. Sample fluid is transferred from the sample cups to an analysis slide using a pipetting device coupled to the pipette tips.

Yet another example of a sample and reagent carrier is U.S. Pat. No. 4,298,570 (Lillig). Lillig's device includes a tray section that has a plurality of wells. The tray section is carried by a turntable, which also receives sample containers. A sample is pipetted from a sample container into a well in the tray section, where additional dilutions of the sample are made. The diluted samples are then taken by an automated pipette to a reaction cell for analysis.

System throughput, that is the number of samples that can be analyzed per unit time, is an important consideration in automated systems. Some of the factors affecting system throughput are number of steps in the process, the processing time for each step, and the number of steps in process at any one time.

Sample carrying devices, such as those of Tersteeg et al. and Lillig, are adapted to steps involved in the processing of individual distinct samples. In addition, it is often desirable, and sometimes mandatory, that individual sample fluids be automatically diluted with a suitable diluting agent before they are transferred to reaction cells for analysis. Thus, the utilization of these devices is often accompanied by multiple fluid aspiration and dispense cycles. These can be time consuming, especially when an analyzer is equipped with a single pipetting device or dispenser probe.

The application (Ser. No. 08/048,708 filed Apr. 16, 1993, now U.S. patent application Ser. No. 08/072,202 and now U.S. Pat. No. 5,356,525 issued Oct. 18, 1994) entitled "Sample Handling System", and identified above (and which is not admitted to be prior art with respect to the present invention by its mention in this Background), describes a novel and inventive system, which is useful with a sample device or segment that is moved about by the system to accomplish the required analysis.

Another concurrently filed application (Ser. No. in 08/048,716 filed Apr. 16, 1993, now U.S. patent application Ser. No. 08/071,831 filed on Jun. 3, 1993, now abandoned) incorporated by reference herein entitled "Sample Segment", and identified above (and which is not admitted to be prior art with respect to the present invention by its mention in this Background), discloses a uniquely adapted sample device or segment that is moved about by the aforementioned system to accomplish the required analysis. The sample segment includes a plurality of sample wells that can contain mixing elements and a sealing cover.

The system and sample segment, cited above, are adapted to be used in a capillary electrophoresis analyzer that performs, for example, immunosubtraction capillary electrophoresis analyses. Such analyses often require identical solutions to be distributed to multiple capillaries, for instance, during the wash and run cycles. Thus, the use of multi-well sample segments is unnecessary for these steps Furthermore, the multiple fluid dispensing cycles required to load the individual wells with reagent contribute time consuming steps that decrease system throughput.

Thus, there is a need for a reagent reservoir that is suitable for use in an analyzer where the reservoir is transported within the analyzer to accomplish a desired analysis. Ideally, the reservoir minimizes the number and duration of liquid dispensing cycles that are necessary to provide reagents to multiple capillaries. A particularly useful reagent-carrying device would also be self-aligning and self-retaining when positioned relative to various operational units of an automated analyzer, such as a holding means, transport arm, or latching mechanism.

SUMMARY

The reagent segment described in this application satisfies the need for such a transportable reservoir. In one form of the present invention, the reagent segment includes an elongated flange-like body with an open continuous trough formed within the flange. The trough is sufficiently long and wide to receive multiple capillaries as well as a dispenser probe. To facilitate the accumulation of liquid, the floor of the trough is sloped towards a drainage zone, which is the deepest portion of the trough.

Additionally, the reagent segment can include curved opposite edges and the trough can be formed along an arc defined between such edges.

In another aspect of the present invention, the reagent segment is structured for use in conjunction with a transport means. The segment may include a body, a trough, and at least two protrusions on the exterior wall of the trough that fit within corresponding cavities of a transport arm.

In yet another aspect of the present invention, the reagent segment is adapted for use in conjunction with a latching mechanism. The segment includes a body, a trough, and a protuberance on the exterior surface of the trough that is shaped to conform to a hole in the latching mechanism.

Further, the reagent segment can include at least one indexing rib, between the exterior surface of the trough and the rim of the body, that can be inserted within an indexing slot of a holding means. This structural adaptation serves to align and retain the reservoir within the holding means.

The reagent segment can further comprise a concave depression on the interior surface of the trough at the drainage zone. The depression can coincide with the protuberance on the exterior surface of the trough that associates with the hole in the latching mechanism.

In addition, a reagent segment in accordance with the present invention may include various combinations of the features just described.

DRAWINGS

These and other features, aspects, and advantages of the present invention will become better understood with reference to the following description, appended claims, and accompanying drawings wherein:

FIG. 1 is a perspective view of a reagent segment in accordance with the present invention;

FIG. 2 is a section view of a preferred embodiment of the reagent segment of FIG. 1 taken along line 2—2 thereof;

FIG. 3 is a bottom plan view of the reagent segment of FIG. 2;

DETAILED DESCRIPTION

Figure 4:
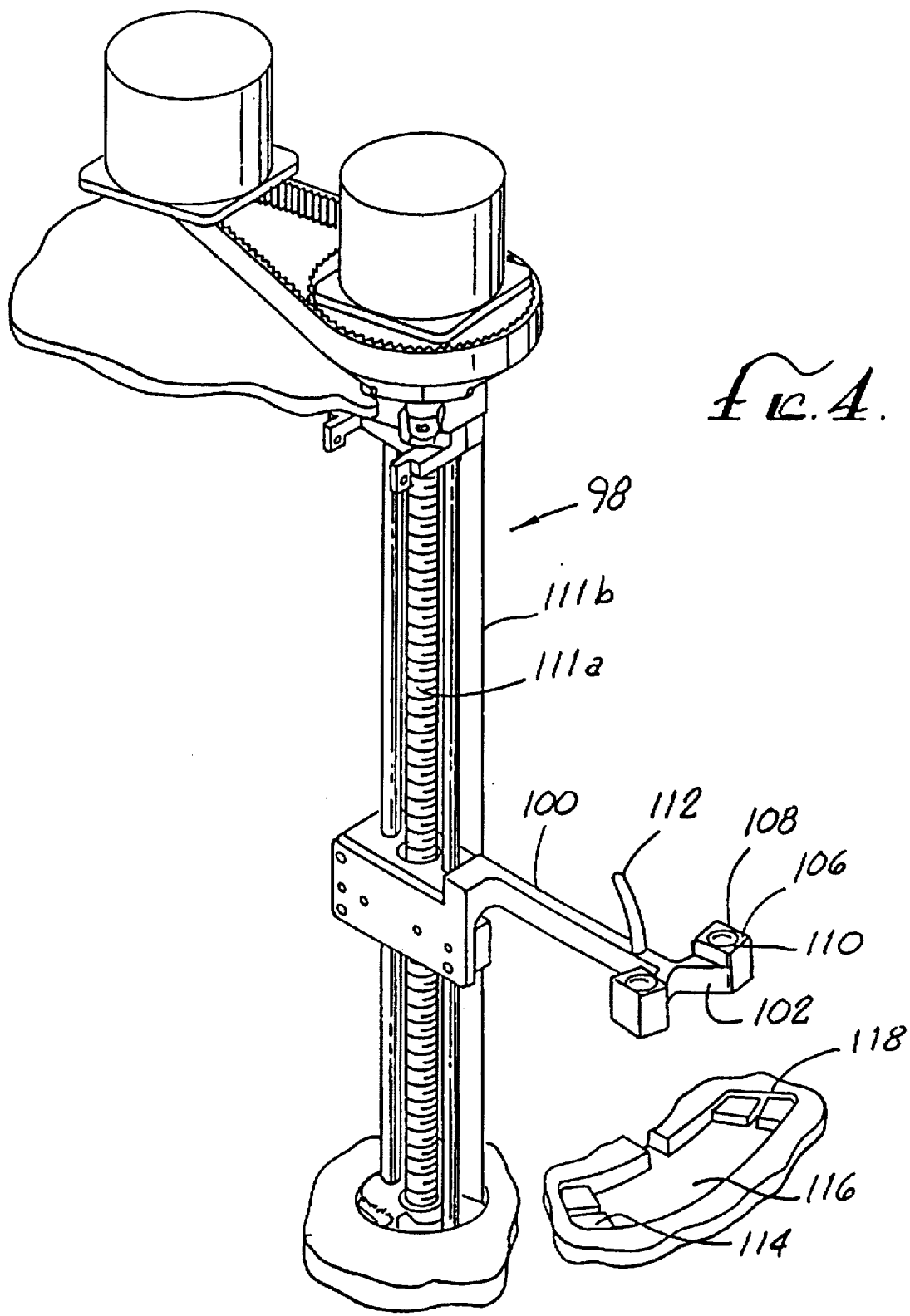
FIG. 4 is a simplified perspective view of a transport means and a holding means with which the reagent segment of FIG. 1 may be used.

Referring to FIG. 1, a reagent segment 10 in accordance with the present invention is defined by a body in the form of a flange 12 and a trough 30. The flange 12 is generally arcuate, having curved opposite edges 16a and 16b and an arcuate center line 17. The flange has ends 18a and 18b that are generally perpendicular to the longitudinal axis or center line 17 and rounded corners 22a, 22b, 22c, and 22d.

Depending lips 24a and 24b and depending sides 26 are formed around the periphery of the flange 12, the lips 24a and 24b being proximate the ends 18a and 18b and the sides being formed along most of the lengths of the edges 16a and 16b. Each of the sides 26 includes two legs 28 suitable for supporting the sample segment 10 on a flat surface.

In the embodiment disclosed herein, a trough 30 is defined in the reagent segment 10. The trough 30 lies on the arcuate center line 17 and defines an elongated curved opening 32 (FIG. 2) in the flange 12. The trough 30 has an interior volume 34 defined by a tapered interior wall surface 36 and a sloping interior bottom surface 38. The deepest portion of the interior bottom surface 38 defines a drainage zone 40, which comprises a rounded concave depression 42. A rounded protuberance 52 or latch knob extends out from the site on the exterior surface 50 that coincides with the interior concave indentation 42. In a preferred embodiment of the reagent segment 10 the protuberance 52 has a hollow center that forms an aperture 53 at the distal end of the protuberance.

Figure 5:
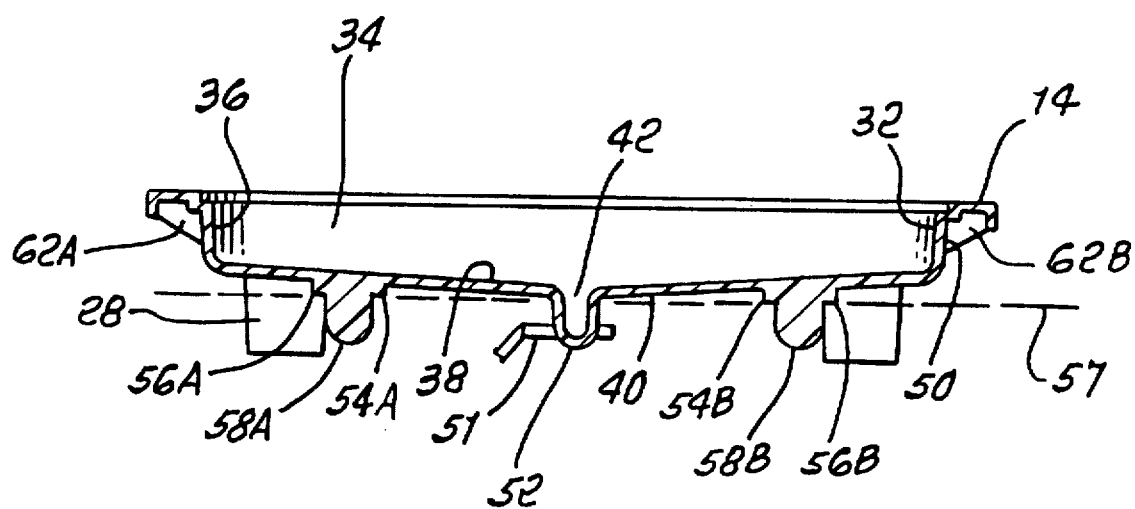
FIG. 5 is a section view of a second embodiment of the reagent segment of FIG. 1 taken along line 2—2 thereof.

The exterior surface 50 generally mirrors the shape of the interior surfaces of the trough with the exception of two protrusions 54a and 54b (FIG. 5) or 55a and 55b (FIG. 2). In the preferred embodiment (FIG. 2) 55a and 55b are conical protrusions with hollow cores that form openings 59a and 59b at the distal ends of the protrusions. In a second embodiment (FIG. 5) the cylindrical wall portions 54a and 54b define annular flat surfaces or shoulders 56a and 56b.

The flat surfaces 56a and 56b together define a plane 57 that is generally parallel to the flange 12. The annular flat surfaces 56a and 56b encircle rounded exterior ends 58a and 58b. As can be seen with reference to FIG. 5, annular flat surfaces 56a and 56b are substantially midway between the floor of the trough 38 and the rounded ends 58a and 58b.

Figure 6:
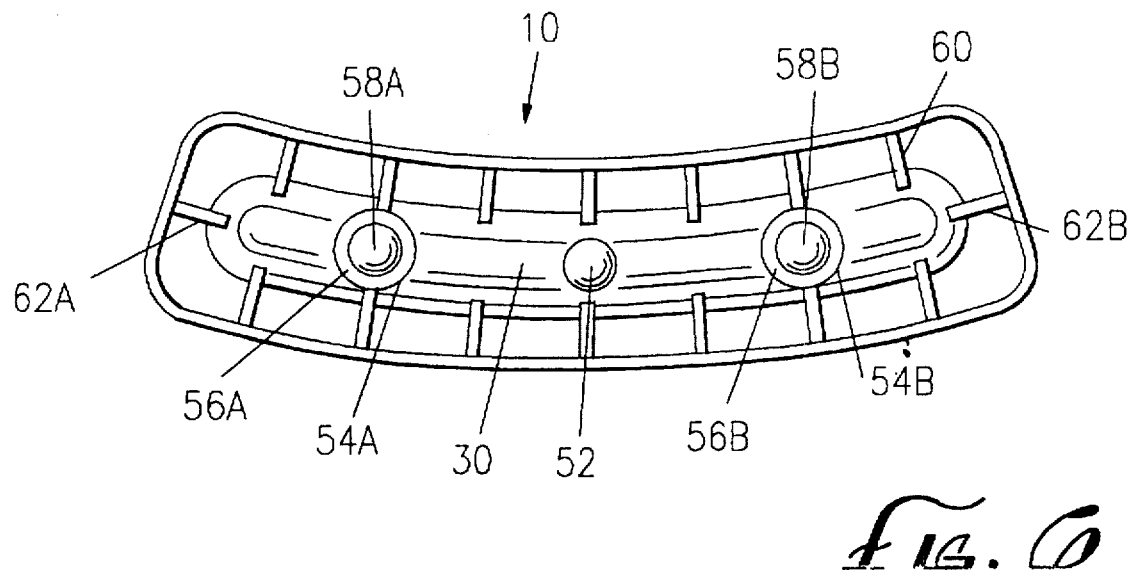
FIG. 6 is a bottom plan view of the reagent segment of FIG. 5.

Reinforcing ribs 60 (FIGS. 3 and 6) are formed between the trough 30 and depending sides 26 adding strength and rigidity to the reagent segment 10. Indexing ribs 62a and 62b (FIGS. 2, 3, 5 and 6) are formed proximate the ends 18a and 18b between the rim 14, lips 24a and 24b and the exterior surface 50 of trough 30, and are generally triangular in shape. The indexing ribs 62a and 62b are used to locate or index the reagent segment 10 with respect to supports 114 of an automated analyzer or capillary electrophoresis apparatus, on which the reagent segment 10 may be used as is described with reference to FIG. 4.

The reagent segment 10 can be formed from a polymeric material such as high density polyethylene, via injection molding. It is useful with an automated transport means 98 (FIG. 4), which receives and removably retains the reagent segment 10, preferably by means of the conical protrusions 55a and 55b. Alternatively, flat surface 56a and 56b and rounded exterior ends 58a and 58b on the exterior surface 50 are received and retained by the transport means. Such an automated transport means 98 can include, for example, an arm 100 with forks or projections 102 at one end thereof. The projections 102 carry flexible boots 106 that include sealing upper rims 108 and interiors 110 shaped to conform to the conical protrusions 55a and 55b or the rounded exterior ends 58a and 58b. The interiors 110 are connected to tubing 112, which is in turn connected to a controllable source of vacuum. The boots 106 and interiors 110 are spaced to align with the conical protrusions 55a and 55b or rounded exterior ends 58a and 58b. The automated transport means 98 also may include means, such as a lead screw 111a and spindle 111b, for rotational and vertical displacement of the arm 100.

The automated analyzer also includes holding means for the reagent segment 10 having supports 114 upon which the ends 18a and 18b are supported with an open area 116 through which the projections 102 can be raised. Slots 118 in the supports 114 are spaced and sized to receive the indexing ribs 62a and 62b, thus indexing or accurately positioning the reagent segment 10 with respect to the open area 116 and thus the automated transport means 98.

The reagent segment 10 can be used to service multiple capillaries in parallel during the washing or running steps of an automated capillary electrophoresis procedure. Providing a greater volume of homogeneous reagent during these steps minimizes the number of repetitive aspirate/dispense cycles required to adequately distribute reagent to the capillaries.

To retrieve and removably retain the reagent segment 10 during a typical reagent distribution cycle, the reagent segment 10 is disposed on the holding means and the boots 106 are aligned with the protrusions 54a and 54b or 55a and 55b. The arm 100 is moved upwardly to receive either the conical protrusions 55a and 55b or the rounded exterior ends 58a and 58b and the annular flat surfaces 56a and 56b. Vacuum is applied via the tubing 112, holding the reagent segment 10 in place. Conversely, the reagent segment 10 can be deposited at the supports 114 by lowering the arm 100 through the open area 116 until the reagent segment is indexed by the indexing ribs 62a and 62b engaging the slots 118 and the reagent segment 10 comes to rest on the supports 114, releasing the vacuum, and further lowering the arm 100.

When the reagent segment 10 is engaged by the arm 100, it can be transported to a dispenser probe (not shown) for the addition and removal of fluid. The arm 100 is rotated horizontally about a vertical axis, the boots 106 following a constant radius path about the vertical axis. Preferably, an arc of such a path matches the arcuate center line 17 of the flange 12.

To secure the reagent segment 10 in proximity to the capillaries of an automated capillary electrophoresis apparatus (not shown), the arm 100 of the transport means 98 carrying the reagent segment 10 is rotated horizontally about a vertical axis to align the opening of the trough 32 with the multiple capillaries of the apparatus. The arm 100 is then moved upwardly until the flange 12 is proximate the capillaries. A latching mechanism 51 then engages the segment 10 via a valve that brings a hole, spaced and sized to conform to the latch knob 52, proximate the protuberance 52 so that it retains the segment 10 next to the capillaries. The transport means 98 is then withdrawn by releasing the vacuum, and lowering arm 100. Following the completion of a washing or analytical step, the reagent segment is removed by reversing the mechanical process.

Thus, a reagent segment 10 in accordance with the present invention is particularly and uniquely adapted for (1) alignment and retention within a holding means, (2) retrieval and transfer via a mechanized transport apparatus, (3) channeling, pooling, and draining reagents, (4) conveying a quantity of reagent to the site of analysis, (5) securing a reservoir of reagent in close proximity to the capillaries, and (6) providing a quantity of homogeneous fluid to multiple outlets. The advantages of these individually inventive aspects of the present invention are apparent, and further advantages are evident by combinations of such aspects.

While the segment 10 is referred to herein as a reagent segment, it is clear that the segment 10 is also useful for various solutions that can be used in analysis. Thus, the word "reagent" is to be read and interpreted broadly to include but not be limited to, for example, liquid samples, diluents, buffers, and solutions. Therefore, the spirit and scope of the appended claims should not be limited to the description of the preferred versions contained herein.

What is claimed is:

1. In an automated capillary electrophoresis apparatus comprising multiple capillaries, a dispenser probe for dispensing reagent into a reagent segment and transport means having at least two cavities, the improvement comprising a reagent segment for feeding reagent to the multiple capillaries of the automated capillary electrophoresis apparatus wherein the reagent segment comprises:
   a) an elongated body;
   b) an elongated, open, continuous trough in the body, the trough having a floor and being sufficiently long and wide to simultaneously receive multiple capillaries of the automated analyzer;
   c) a drainage zone in the floor of the trough, the drainage zone being deeper than the remainder of the trough with the floor of the trough sloping toward the drainage zone so reagent can be substantially completely removed from the trough by aspiration; and
   d) a fill section in the trough sufficiently wide to receive the dispenser probe.

2. A reagent segment as in claim 1, wherein the body is arc shaped.

3. A reagent segment as in claim 1, wherein the trough has a longitudinal axis and the drainage zone is located midway along the longitudinal axis of the trough.

4. A reagent segment as in claim 1, wherein the automated analyzer includes transport means having at least two cavities, and the trough further comprises an internal wall and an external wall, the external wall having at least two protrusions, the protrusions being spaced and sized to be received within the cavities of the transport means.

5. A reagent segment as in claim 1, wherein the automated analyzer includes a latching mechanism having at least one hole for securing the reagent segment body in proximity to the capillaries, the trough further comprising an internal wall and an external wall, the external wall having a protuberance, the protuberance being shaped to conform with the hole of the latching mechanism.

6. In an automated capillary electrophoresis apparatus comprising multiple capillaries, a dispenser probe for dispensing reagent into a reagent segment and transport means having at least two cavities, the improvement comprising a reagent segment for feeding reagent to the multiple capillaries of the automated capillary electrophoresis apparatus wherein the reagent segment comprises:
   a) an elongated body;
   b) an elongated, open, continuous trough formed in the body, having an interior surface and an exterior surface, the trough being sufficiently long and wide to receive the multiple capillaries;
   c) a drainage zone formed in the interior surface of the trough, the drainage zone being deeper than the remainder of the trough so reagent can be removed from the trough by aspiration;
   d) a fill section in the trough being sufficiently wide to receive a dispenser probe; and
   e) the exterior surface of the trough having at least two protrusions, the protrusions being spaced and sized to be received within the cavities of the transport means.

7. A reagent segment as in claim 6, wherein the body is arc shaped.

8. A reagent segment as in claim 6, wherein the interior surface of the trough slopes towards the drainage zone so reagent can be substantially completely removed from the trough by aspiration.

9. A reagent segment as in claim 6, wherein the interior surface of the trough has a concave indentation at the drainage zone.

10. A reagent segment as in claim 6, wherein the reagent segment has a longitudinal axis and the drainage zone is located midway along the longitudinal axis of the segment.

11. A reagent segment as in claim 6, wherein each protrusion is conical, and each protrusion has a hollow core with an opening to the distal end of the protrusion.

12. A reagent segment as in claim 6, wherein the at least two protrusions are cylindrical with annular flat surfaces encircling rounded ends, the annular flat surfaces being midway between the trough opening and the rounded ends.

13. A reagent segment as in claim 6, wherein the body has a rim and at least one indexing rib between the exterior surface of the trough and the rim of the body.

14. A reagent segment as in claim 13, further comprising a second indexing rib between the exterior surface of the trough and the rim of the body.

15. In an automated capillary electrophoresis apparatus comprising multiple capillaries and a latching mechanism having at least one hole for securing a reagent segment in proximity to the multiple capillaries, the improvement comprising a reagent segment for feeding reagent to the multiple capillaries of the automated capillary electrophoresis apparatus wherein the reagent segment comprises:

a) an elongated arcuate body;

b) an elongated, open, continuous trough formed in the body, the trough having an interior surface and an exterior surface, sufficiently long and wide to receive the multiple capillaries;

c) a drainage zone formed in the interior surface of the trough, the drainage zone being deeper than the remainder of the trough, the interior surface of the trough being tapered from wide to narrow in the direction toward the drainage zone so reagent can be substantially completely removed from the trough by aspiration;

d) a fill section in the trough, the fill section being sufficiently wide to receive the dispenser probe; and e) a protuberance on the exterior surface of the trough, the protuberance being shaped to conform with the hole of the latching mechanism.

16. A reagent segment as in claim 15, wherein the interior surface of the trough has a concave depression at the drainage zone.

17. A reagent segment as in claim 16, wherein the concave depression in the interior surface of the trough coincides with the protuberance on the exterior surface of the trough.

18. A reagent segment as in claim 17, wherein the reagent segment has a longitudinal axis and the drainage zone is located midway along the longitudinal axis of the segment.

19. In an automated capillary electrophoresis apparatus comprising multiple capillaries and a latching mechanism having at least one hole for securing a reagent segment in proximity to the multiple capillaries, the improvement comprising a reagent segment for feeding reagent to the multiple capillaries of the automated capillary electrophoresis apparatus wherein the reagent segment comprises:

a) an elongated arcuate body;

b) an elongated, open, continuous trough formed in the body, the trough having an interior surface and an exterior surface, sufficiently long and wide to receive the multiple capillaries;

c) a drainage zone formed in the interior surface of the trough, the drainage zone being deeper than the remainder of the trough, the interior surface of the trough being tapered from wide to narrow in the direction toward the drainage zone so reagent can be substantially completely removed from the trough by aspiration;

d) a concave depression on the interior surface of the trough at the drainage zone;

e) a protuberance on the exterior surface of the trough, the protuberance being shaped to conform with the hole of the latching mechanism; and f) the concave depression in the interior surface of the trough coincides with the protuberance on the exterior surface of the trough.

20. A reagent segment useful with an automated capillary electrophoresis apparatus wherein the apparatus includes multiple capillaries, a dispenser probe for dispensing reagent, transport means having at least two bores with vacuum means for controllably applying a vacuum to the bores, holding means with at least one indexing slot, and a latching mechanism having at least one hole for securing the segment in proximity to the capillaries, the reagent segment comprising:

a) an elongated arcuate body with a rim;

b) an elongated, open, continuous trough formed in the body, the trough having a floor, an interior surface, and an exterior surface, the trough being sufficiently long and wide to receive the multiple capillaries;

c) a drainage zone in the floor of the trough, the drainage zone being deeper than the remainder of the trough, with the floor of the trough sloping towards the drainage zone so reagent can be substantially completely removed from the trough by aspiration;

d) a fill section in the trough, the fill section being sufficiently wide to receive the dispenser probe;

e) the interior surface of the trough being tapered from wide to narrow in the direction toward the drainage zone and having a concave indentation at the drainage zone;

f) a latch knob on the exterior surface of the trough at the drainage zone, the latch knob being shaped to conform with the hole of the latching mechanism and at least two conical protrusions on the exterior surface of the trough, the conical protrusions each having a hollow core with an opening to the distal end of the protrusion, the protrusions being spaced and sized to be received within the bores of the transport means; and g) at least one indexing rib located between the exterior surface of the trough and the rim of the body, the rib being capable of insertion within the indexing slot of the holding means.

\* \* \* \* \*